United States Patent [19]

Cox et al.

[11] Patent Number: 5,496,493
[45] Date of Patent: Mar. 5, 1996

[54] ULTRA MILD PERSONAL CLEANSING BAR CONTAINING SMALLER-SIZED PARTICULATE WAX

[75] Inventors: Sherri V. Cox, West Chester; Monica B. Emelko, Cincinnati, both of Ohio

[73] Assignee: The Procter & Gamble Company, Cincinnati, Ohio

[21] Appl. No.: 241,077

[22] Filed: May 10, 1994

[51] Int. Cl.$^6$ ............................... C11D 17/00; C11D 9/22
[52] U.S. Cl. ..................... 252/174; 252/123; 252/128; 252/130; 252/134; 252/DIG. 5; 252/DIG. 16
[58] Field of Search .................. 252/108, 128, 252/549, 173, 174, 174.11, 174.23, DIG. 16, 123, 130, 134, DIG. 5

[56] References Cited

U.S. PATENT DOCUMENTS

| | | | |
|---|---|---|---|
| 2,714,093 | 7/1955 | Blumenthal | 252/DIG. 16 |
| 2,734,870 | 2/1956 | Lewis | 252/DG. 16 |
| 3,376,229 | 4/1968 | Haass et al. | 252/DIG. 16 |
| 3,766,097 | 10/1973 | Rosmarin | 252/DIG. 16 |
| 3,989,647 | 11/1976 | Prince | 252/DIG. 16 |
| 4,180,470 | 12/1979 | Tokosh et al. | 252/DIG. 16 |
| 4,231,904 | 11/1980 | Machin | 252/DIG. 16 |
| 4,695,395 | 9/1987 | Caswell et al. | 252/DIG. 16 |
| 4,812,253 | 3/1989 | Small et al. | 252/DIG. 16 |
| 4,820,447 | 4/1989 | Medcalf et al. | 252/117 |
| 4,913,828 | 4/1990 | Caswell et al. | 252/547 |
| 4,954,282 | 9/1990 | Rys et al. | 252/117 |
| 5,024,777 | 6/1991 | Smith et al. | 252/DIG. 16 |
| 5,091,272 | 2/1992 | Treger | 429/62 |
| 5,154,849 | 10/1992 | Visscher et al. | 252/174.15 |
| 5,204,014 | 4/1993 | Redd et al. | 252/117 |
| 5,211,870 | 5/1993 | Gilbert et al. | 252/120 |
| 5,258,063 | 11/1993 | Cifuentes et al. | 106/3 |
| 5,294,363 | 3/1994 | Schwartz et al. | 252/108 |

FOREIGN PATENT DOCUMENTS 0189332 7/1986 European Pat. Off. .
5634797 4/1987 Japan .

Primary Examiner—Paul Lieberman
Assistant Examiner—Caroline L. Dusheck
Attorney, Agent, or Firm—Tara M. Rosnell; Leonard Williamson

[57] ABSTRACT

The present invention encompasses an ultra mild personal cleansing bar that contains small sized solid wax particles of which from 85% to 100% are less than 16 microns in size. Preferably 90% to 100% of the wax particles are from 0.1 to 15 microns in size, and more preferably they are from 0.1 to 10 microns in size. The smaller-sized solid wax particles of the present invention provide better mildness than comparable personal cleansing bars which contain larger wax particles. These smaller wax particles do not negatively impact bar in-use aesthetics, for example, bar lather.

12 Claims, No Drawings

ULTRA MILD PERSONAL CLEANSING BAR CONTAINING SMALLER-SIZED PARTICULATE WAX

TECHNICAL FIELD

The present invention relates to personal cleansing products containing solid waxes.

BACKGROUND OF THE INVENTION

This invention relates to improved mild skin cleansing bars. The cleansing of skin with surface-active cleansing preparations has become a focus of great interest. Many people wash and exfoliate their skin with various surface-active preparations several times a day. Ideal skin cleansers should cleanse the skin gently, causing little or no irritation, without defatting and overdrying the skin or leaving it taut after frequent routine use. Most lathering soaps, liquids and bars included, fail in this respect.

Synthetic detergent bars, frequently referred to as "combo bars" and/or "syndet bars," are known and are becoming increasingly popular. However, widespread replacement of soap bars by syndet bars has not so far been possible for a variety of reasons, primarily the poor physical characteristics of syndet bars as compared to soap bars, e.g., smear or bar messiness, off odors, poor processability, stickiness, brittleness,, lather quality or combinations thereof.

One object of the present invention is to deliver an ultra mild personal cleansing bar without impairing good lathering properties. Yet another object of the present invention is to provide a good lathering bar without impairing mildness. Other objects of the present invention will be apparent in the light of the following disclosure.

SUMMARY OF THE INVENTION

The present invention encompasses an ultra mild personal cleansing bar that contains solid wax particles of which from 85% to 100% are less than 16 microns. The wax particles are preferably from 0.1 to 15 microns in size, and more preferably from 0.1 to 10 microns in size. The smaller-sized solid wax particles of the present invention provide better mildness than comparable personal cleansing bars which contain larger wax particles. These smaller wax particles do not negatively impact bar in-use aesthetics, for example, bar lather.

DETAILED DESCRIPTION OF THE INVENTION

The present invention encompasses a personal cleansing product that contains smaller-sized solid wax particles than those heretofore used, particularly in mild personal cleansing bars as disclosed herein. The present invention provides better mildness than prior art personal cleansing bars which contain larger wax particles. These smaller wax particles of the present invention do not negatively impact in-use aesthetics, for example bar lather.

The present invention encompasses a personal cleansing bar that contains solid wax particles of which 85% are less than 16 microns. Preferably 90 % are less than 16 microns. The wax particles are preferably from 0.1 to 15 microns in size, and more preferably from 0.2 to 10 microns in size.

The bar of the present invention can be made by several methods. Preferred methods include mixing molten and/or solubilized ingredients at elevated temperatures (greater than 120° F./49° C.) and with moistures (greater than 20% moisture). Processing methods include atmospheric flash or vacuum drying followed by traditional milling/plodding operations, atmospheric flash or vacuum drying followed by scrapped wall heat exchangers (also known as freezers), or by traditional framing operations.

General compositions encompassing this invention comprise three key ingredients: lathering surfactant, a plasticizer and a binder. Some high and low levels of these ingredients in functional limits are set out below in Table A in parts by weight of the bar.

The term "lathering surfactant" as used herein and further defined hereinafter, means one which lathers better than the long chain sodium $C_{16}$–$C_{18}$ alkyl sulfate.

The term "Plasticizer" as used herein means any material that is solid at room temperature, but is malleable at bar plodding processing temperatures of 35° C. to 46° C. (95° F. to 115° F.). This is the temperature of the plasticizer. At least 5 parts by bar weight is said solid wax.

The term "Binder" as used herein means any material that is by itself liquid, at room temperature and selected from water and liquid polyols. The water and liquid polyol can have a ratio of 20:1 to 1:5; or 5:1 to 1:3 or 2:1 to 1:2. Their levels in the bar are 3–30 parts with 3–30 parts water and zero to 15 parts polyol, etc.

TABLE A

| Key Components | Key Components*** | | |
| --- | --- | --- | --- |
|  | High | Low | Comments |
| Lathering Surfactant - 20 parts to 90 parts. | Brittleness 70 parts–90 parts | Lather 20 parts–30 parts | Assumes trade-off vs. plasticizer |
| Plasticizer - 10 parts to 50 parts* Binder** | Lather Stickiness, Smear | Brittleness Brittleness, Lather |  |

*Plasticizer comprised of a solid aliphatic materials, e.g. fatty acids, fatty alcohols, paraffins, other waxes, monoglycerides, diglycerides, triglycerides, alkaline soaps; or high molecular weight (solid) hydrophilic materials, e.g. polyethylene glycols, polypropylene glycols; starches, sugars and/or mixtures thereof.
**Binder - includes water and low molecular weight (liquid) materials, e.g. liquid polyols.

TABLE A-continued

Key Components***

| Key Components | High | Low | Comments |
|---|---|---|---|

*** Referring to Table A, when the level of surfactant is low, that is, from 20 parts to 30 parts by weight of the bar, the ratio of synthetic surfactant to other lathering soaps is preferably from 1:2 to 1:8; preferably 1:3 to 1:6. This ratio is needed to provide acceptable bar lather. Referring to Table A, when the level of surfactant is high, that is, from 70 parts to 90 parts, the ratio of it to plasticizer (plastic materials) is preferably from 1.4:1 to 9:1. This ratio is needed to avoid unacceptable brittleness.

TABLE B

SOME KEY INGREDIENTS OF THIS INVENTION ARE SUMMARIZED IN TABLE B IN PARTS BY WEIGHT OF THE BAR.

| Component in Parts* | Full Range | Preferred | More Preferred |
|---|---|---|---|
| A. Sodium Acyl Isethionate | 0 to 70 | 10 to 60 | 15 to 50 |
| B. Na-Alkyl Glyceryl Ether Sulfonate | 0 to 70 | 5 to 50 | 10 to 40 |
| C. Na-Acyl Sarcosinate | 0 to 25 | 1 to 20 | 2 to 15 |
| D. Na-Cetearyl Sulfate | 0 to 50 | 1 to 45 | 2 to 40 |
| E. Na-soap | 0 to 25 | 1 to 20 | 2 to 15 |
| F. Mg-soap | 0 to 50 | 1 to 30 | 2 to 25 |
| G. Fatty Acid | 0 to 35 | 0.5 to 25 | 1 or 2 to 20 |
| H. Paraffin | 5 to 50 | 5 to 45 | 5 to 30 or 40 |
| I. NaCl | 0 to 5 | 0.1 to 3 | 0.2 to 2 |
| J. Na2SO4 | 0 to 5 | 0.1 to 3 | 0.2 to 2 |
| K. Na-Isethionate | 0 to 15 | 0.1 to 10 | 0.2 to 8 |
| L. Water | 3 to 30 | 4 to 20 | 5 to 10 |
| M. Fragrance | 0 to 2 | 0.5 to 1.5 | 0.8 to 1.2 |
| N. Glycerin | 0 to 15 | 1 to 12 | 2 to 10 |

*Sodium Acyl Isethionate (STCI) is a mild lathering synthetic surfactant. A preferred SCI is "STCI" herein defined as "sodium topped coconut isethionate" which is further defined as SCI with alkyl carbon chains having: 0% to 4% of highlyway soluble acyl groups (C6, C8, C10, C18:1 and C18:2); 45–65% C12, and 30–55% C14, C16, C18. The terms SCI and STCI are used interchangeably herein unless otherwise specified.
Sodium Alkyl Glyceryl Ether Sulfonate is a mild lathering synthetic surfactant. It is made from coconut fatty alcohols. Sodium Cetearyl Sulfate is a non-soil load filler and processing aid. Magnesium Soap is a non-soil load filler and processing aid. Sodium Soap is a lather booster and processing aid. Fatty acid is a plasticizer. Paraffin is a plasticizer. Sodium Chloride provides bar firmness and improves bar smear. Sodium sulfate provides bar firmness and improves bar smear. Sodium Isethionate provides bar firmness and improves bar smear. Water is a binder. Fragrance is a binder and improves odor. Glycerin is a binder.

The preferred bar has a pH of from 4 to 10 in a 1 part aqueous solution. The preferred pH is from 5 to 9, more preferably 6 to 8.

The percentages, ratios, and parts herein are on a total composition weight basis, unless otherwise specified. All levels and ranges herein are approximations, unless otherwise specified. Levels of ingredients are expressed herein on a "solids" basis, incorporating all non-water components together, unless otherwise specified.

It is asserted that personal cleansing compositions of this invention that demonstrate the improved mildness via smaller sized wax are not limited to bar form. Liquids and creams which contain the said smaller sized solid wax particles can also be formulated. Therefore, the application of this invention is applicable to personal cleansing liquids and creams.

THE SMALL SIZED PARTICULATE WAX

Critical to the present invention is the small sized particulate wax. It is important that at least 85% to 100% of the wax particles are less than 16 microns in size. This small size can be achieved in a number of different ways. The preferred method is to emulsify the wax in molten form in an aqueous surfactant environment which is then quickly cooled to crystallize the wax particles within the specified particle size ranges.

Without being constrained to theory, it is theorized that the smaller sized solid waxes improve product mildness by providing a larger amount of surface area to which the surfactant will partition. This partitioning reduces the amount and type of surfactant that deposits onto the skin, thus creating less damage than if the smaller sized solid wax was not present. It is also theorized that this smaller sized solid wax plus surfactant system improves lather by increasing the lather film viscosity.

METHOD OF ASSESSING WAX PARTICLE SIZE

WAX PARTICLE SIZE is determined with a Hofiba LA-900 diffraction type analyzer. Three separate detectors measure a particle's side, front, and rear scattering. This allows for particle size determination in the range of 0.05 to 1000 microns. The Mie scattering theory is used as the response function of scattering light.[1] Particles oscillate in the incident field and result in a scattered field. The magnetic and electric multipole moments of the particles contribute to the scattered field.[2]

(1) Horiba LA-900 Instruction Manual, Horiba Instruments Incorporated Irvine, Calif., 1991, Appendix p. 11.
(2) Beeher, Paul. Editor, Encyclopedia of Emulsion Technology, Vol. I, Marcel, Dekker, N.Y., 1984, pp. 458–459.

Personal cleansing liquid emulsions are made using 2.5 parts finished bar material and 97.5 parts tap water. The emulsions are made in a stirred beaker at a constant temperature which is below the melting temperature of the wax particles. The temperature at which the emulsion is made is typically between 100° F. and 120° F. (38°–49° C.), depending on the melting point of the wax selected. The emulsions are then stored at room temperature for at least 2 days. (If the emulsion separates and forms an upper phase which is comprised mostly of wax, as determined by analytical techniques such as X-ray diffraction, the upper phase of the emulsion is then recombined with the continuous phase of the emulsion by agitation before testing.) The particle size of the solid wax in the emulsions is quantitatively determined with the Horiba LA-900 at 90% transmittance. The samples are sonicated to disperse any aggregates so that sizes of individual particles can be determined. The particle size is evaluated based on the Horiba Volume Method (diameter of average volume).

WAX AND OTHER KEY PLASTICIZERS

The preferred plasticizers of the present invention are as follows: (1) fatty acid; (2) the smaller sized wax, preferably paraffin wax. The bar can contain from 10 parts to 50 parts;

more preferably 20 parts to 45 parts; most preferably 30 parts to 40 parts of plastic material selected from the group consisting of: free fatty acid, wax, magnesium soaps, other plasticizer or mixtures thereof.

The fatty acid material which is desirably incorporated into the present invention includes material ranging in hydrocarbon chain length of from 10 to 22, essentially saturated. These fatty acids can be highly purified individual chain lengths and/or crude mixtures such as those derived from fats and oils. The industry term "triple pressed stearic acid" comprises 45% stearic and 55% palmitic acids. Thus, this is its meaning as used herein.

"Insoluble" soaps, e.g., magnesium and zinc soaps, are not included in the level of "sodium soap" in the composition definition. However, insoluble soaps can be used as non-lathering, non-soil-load diluents and processing aids.

The waxes are selected from the group consisting of beeswax, spermaceti, carnauba, bayberry, candelilla, montan, ozokerite, ceresin, paraffin, synthetic waxes such as Fisher-Tropsch waxes, microcrystalline wax, and mixtures thereof.

A highly preferred component of this invention is a wax, preferably paraffin wax having a melting point (M.P.) of from 105° F. to 180° F. (54°–82° C.), preferably from 120° F. to 170° F. (60°–74° C.), and most preferably from 130° F. to 160° F. (61°–71° C). "High melt" paraffin is paraffin that has a melting point of 150°–160° F. (66°–71° C.). "Low melt" paraffin is paraffin that has a melting point of 130°–140° F. (54°–60°). A preferred paraffin wax is a fully refined petroleum wax which is odorless and tasteless and meets FDA requirements for use as coatings for food and food packages. Such paraffins are readily available commercially. A very suitable paraffin can be obtained, for example, from The National Wax Co. under the trade name 6975.

The smaller sized wax, preferably paraffin, is present in the bar in an amount ranging from 5 parts to 50 parts by weight. The wax ingredient is used in the product to impart skin mildness, plasticity, firmness, and processability. It also provides a glossy look and smooth feel to the bar.

SURFACTANTS DEFINED

The term "lathering surfactant" as used herein and further defined hereinafter, means one which lathers better than the long chain sodium C16–C 18 alkyl sulfate.

The composition may include soaps derived from hydrocarbon chain lengths of from approximately 10 to 22 (including carboxyl carbon) and are preferably saturated. It is preferred that the soap be the sodium salt, but other soluble soap can be used. Potassium, ammonium, triethanolammonium, and mixtures thereof, are deemed acceptable. The soaps are preferably prepared by in situ saponification or ion exchange with a halide salt of the corresponding fatty acids, but they may also be introduced as preformed soaps. Either some or all of the soap is preferably precomplexed with cationic polymer, or polymers, when polymer is used.

The isethionates, sarcosinates, and glyceryl ether sulfonates may be pure chain length variants or those derived from commercial oils such as coconut oil. Here, the lauryl chain length should preferably account for at least 20% to as much as 100% of the weight of the given mild surfactant.

Numerous examples of other surfactants in general are disclosed in the patents incorporated herein by reference. They include limited amounts of anionic acyl sarcosinates, methyl acyl taurates, N-acyl glutamates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chains for these other surfactants are $C_8$–$C_{22}$, preferably $C_{10}$–$C_{18}$. Alkyl glycosides and methyl glucoside esters are preferred mild nonionics which may be mixed with other mild anionic or amphoteric surfactants in the compositions of this invention.

The bars of this invention can have from 0 to 10 parts of high lathering, nonmild surfactants and still maintain the preferred mildness requirement of the bar. Examples of these surfactants include linear alkyl benzene sulfonates and shorter chain or traditional (coconut) alkyl sulfates.

A preferred syndet bar can contain a mixture of sodium topped distilled $C_{12}$–$C_{18}$ cocoyl isethionate (STCI) and sodium linear alkylbenzene sulfonate in a ratio of from 35:1 to 15:1, preferably from 30:1 to 20:1.

The Binder

This invention contains water and can contain a liquid water-soluble aliphatic polyol or polyethylene glycol or polypropylene glycol. The polyol may be saturated or contain ethylenic linkages; it must have at least two alcohol groups attached to separate carbon atoms in the chain, and must be water soluble and liquid at room temperature. If desired, the compound may have an alcohol group attached to each carbon atom in the chain. Among the compounds which are effective are ethylene glycol, propylene glycol and glycerine. A preferred polyol is dipropylene glycol, which is effective in amounts as low as 0.1 and 0.25 parts by weight, preferably 0.5 parts to 5 parts; and more preferably from 0.5 parts-2 parts.

Water-soluble polyethylene glycols or water-soluble polypropylene glycols useful in the present invention are those products produced by the condensation of ethylene glycol molecules or propylene glycol molecules to form high molecular weight ethers having terminal hydroxyl groups. The polyethylene glycol compounds may range from diethylene glycol to those having molecular weights as high as 800. Normally, polyethylene glycols having molecular weights up to 800 are liquid and completely soluble in water. As the molecular weight of the polyethylene glycol increases beyond 800, they become solid and less water-soluble. The polypropylene glycol compounds useful in this invention may range from dipropylene glycol to polypropylene glycols having molecular weights of 2000. These are normally liquid at room temperature and are readily soluble in water.

Other Ingredients

The preferred bar of this invention may comprise other cleansing bar ingredients. E.g., it can contain from 0 parts to 5 parts, preferably from 0.3 parts to 1 parts, of a suitably fast hydrating cationic polymer. The preferred polymers have molecular weights of from 1,000 to 5,000,000.

Other ingredients are selected for the various applications. E.g., perfumes can be used in formulating the skin cleansing products, generally at a level of from 0.1 parts to 1.5 parts of the composition. Vegetable oils, such as peanut and soybean oil can be added at levels up to 10 parts, preferably 2 to 6 parts. Alcohols, hydrotropes, colorants, and fillers such as talc, clay, calcium carbonate, oils and dextrin can also be used at appropriate levels. Preservatives, e.g., Irisodium etidronate and sodium ethylenediaminetetraacetate (EDTA), generally at a level of less than 1 part of the composition, can be incorporated in the cleansing products to prevent color and odor degradation. Antibacterials can also be incorporated, usually at levels up to 1.5 parts. Salts, both organic and inorganic, can be incorporated. Examples include sodium chloride, sodium isethionate, sodium sulfate, and their equivalents.

The compositions can also contain an effective, i.e., odor-controlling, amount of various additional zeolite and non-zeolite odor-controlling materials to further expand their capacity for controlling odors, as well as the range of odor types being controlled. Such materials include, for example, cetyl pyridinium chloride, zinc chloride, EDTA, etidronate, BHT, and the like.

The following patents disclose or refer to test methods, methods of making, ingredients and formulations which may be useful in the bars of this invention, and are incorporated herein by reference: U.S. Pat. No. 5,204,014, issued Apr. 10, 1993 to Dunbar et al.; U.S. Pat. No. 5,211,870, issued May 18, 1993 to Cox et al.; U.S. Pat. No. 5,294,363, issued Mar. 15, 1994 to Dunbar et al.; U.S. Pat. No. 4,812,253, issued Mar. 14, 1989 to Small et al.; U.S. Pat. No. 4,820,447, issued Apr. 11, 1989 to Medcalf et al.; U.S. Pat. No. 4,954,282, issued Sep. 4, 1990 to Rys et al.; and U.S. Pat. No. 5,154,849, issued Oct. 13, 1992 to Visscher, et al.

A Method of Making Bars

Crutching (A, B and C are Alternative Procedures)

A.

1. If used, add melted cetearyl sulfate, and/or AGS (50°–75° C.); begin agitation.
2. If used, add NaCl, then $TiO_2$, then EDTA, then etidronate, and then zeolite, and bring crutcher mixture to 85° C. under agitation.
3. Add pre measured caustic and $Mg(OH)_2$, if used, and continue to mix well.
4. Steam sparge to 85° C. before adding remaining ingredients.
5. Add fatty acid and mix for 5–10 minutes at 85° C.
6. Add the paraffin, acyl isethionate, SI and continue mixing for approximately 15–30 minutes while maintaining the mix temperature at 85° C.
7. If used, add glycerin and/or vegetable oil under constant agitation.

B.

1. Add paraffin, acyl isethionate, SI and begin agitation while maintaining the temperature at 85° C.
2. If used, add molten cetearyl sulfate, and/or AGS, (50°–75° C.) and maintain agitation and recirculation.
3. If used, add NaCl, then $TiO_2$ then EDTA, then etidronate, and then zeolite, increasing the temperature in the 85° C. range under agitation and steam sparging.
4. Add the pre measured caustic and $Mg(OH)_2$, if used, and continue to mix well.
5. Add the required fatty acid and mix for another 10 minutes at 85° C. Check for uniform consistency of the crutcher batch.
6. If used, add glycerin and/or vegetable oil under constant agitation.

C.

1. If used, add molten cetearyl sulfate, AGS (50°–75° C.) to the crutcher and begin agitation.
2. Add the paraffin, sodium topped, acyl isethionate, sodium isethionate (SI) and continue to mix with agitation and begin recirculation.
3. If used, add NaCl, then $TiO_2$, then EDTA, then etidronate, and then zeolite, increasing the temperature to 85° C. while agitating and recirculating and steam sparging.
4. Add the pre measured caustic and $Mg(OH)_2$, if used, and continue to mix
5. Add the required fatty acid and mix for another 10 minutes at 85° C. Check for uniform consistency of the crutcher batch and continue to mix until fluid and lump free. 6. If used, add glycerin and/or vegetable oil slowly under constant agitation.

Techniques that Facilitate Making Small-sized Particulate Wax (Paraffin).

Emulsification of the wax can be used at any appropriate point in processing. The use of high shear mixers, crutcher agitation, etc. can be applied. Additionally, premixes and orders of addition that facilitate smaller sized wax emulsification can also be used. For example, pre-mixing the wax with fatty acids and/or fatty alcohols will facilitate smaller sized wax emulsification.

Drying

The crutcher mix can be dried and cooled using a combination flash chamber and chill roll or chill belt. The crutcher mix is first heated to approximately 265°–275° F. (130°–135° C.) by a heat exchanger and then flash dried in a chamber above the chill roll or chill belt. The chill belt or chill roll provides a uniform, thin cool (85°–95° F.; 29°–35° C.) product in flake or chip form. Typical moisture for the flake is from 3 parts to 15 parts, preferably from 5 parts to 10 parts.

Amalgamating

The flakes are weighed and added to a batch amalgamator to obtain uniform flake size and a course mixture of additives that may be brought into the flake mixture (syndet or soap).

Milling

The 3-roll soap mills are set up with the first roll at ~120° F. (49° C.), the second roll at ~100° F. (38° C.), and the final roll at ~68° F. (20° C.). The material is passed through the mills several times to provide a homogeneous mixture of perfume and dried flakes. Typically the milled material has a temperature of 44° to 54° C.

Plodding and Stamping

The plodder is set up with the barrel temperature at 115° F. (46° C.) and the nose temperature at 114°–122° F. (45°–50° C.). The ide is a dual stage plodder that allows use of a vacuum of 15–25 inches (38–64 cm) of Hg. The plugs should be cut in 5 inch (13 cm) sections and stamped with a cold die block using die liquor such as alcohol, if appropriate.

Bar Assessments

The techniques for laboratory assessment of the finished bar properties, e.g., mildness and lather, etc., are set out in the literature. See U.S. Pat. No. 5,204,014, issued Apr. 10, 1993 to Dunbar et al.; U.S. Pat. No. 5,211,870, issued 5/18/93 to Cox et al.; U.S. Pat. No. 5,294,363, issued Mar. 15, 1994 to Dunbar et al.; U.S. Pat. No. 4,812,253, issued Mar. 14, 1989 to Small et al.; and U.S. Pat. No. 4,820,447, issued Apr. 11, 1989 to Medcalf et al.

EXAMPLES AND FORMULAS

The following examples and formulas are illustrative and are not intended to limit the scope of the invention. The methods of making personal cleansing bars are well known. All levels and ranges, temperatures, results, etc. used herein are approximations unless otherwise specified. Therefore, the percentages do not necessarily add up to 100 parts. All component levels are percentages based on weight.

than 16 microns in size. It is 0.25 units less drying than C. E. 1 and 0.07 units less reddening than C. E. 1 in clinical mildness testing. The dryness result is significant with a p-value less than or equal to 0.10.

Experimental Example 3 is similar in composition to Example 2 but has 17 parts sodium acyl isethionate in place of 17 parts sodium alkyl glyceryl ether sulfonate. More than 40% of the wax particles have a size which is greater than 16 microns. The wax particles in Experimental Example 3 are larger than Example 2. Experimental Example 3 is 0.07 units more drying than C. E. 1 and 0.05 units more reddening

TABLE C

| Component | C.E. 1 | Ex. 2 | E.E. 3 | Ex. 4 | Ex. 5 |
|---|---|---|---|---|---|
| Na-Acyl Isethionate | 50 | — | 17 | 17 | 28 |
| Na-Alkyl Glyceryl Ether Sulfonate[1] | — | 34 | 17 | 17 | 16 |
| Na-Linear Alkyl Benzene Sulfonate | 2 | — | — | — | — |
| Na-soap | 12 | 5 | 5 | 3 | 4 |
| Mg-soap | — | 17 | 17 | 17 | 10 |
| Free Fatty Acid | 25 | 9 | 9 | 3 | 4 |
| Paraffin | — | 17 | 17 | 17 | 17 |
| Na-Isethionate | 6 | 1 | 1 | 5 | 3 |
| Glycerin | — | 4 | 4 | 4 | 8 |
| Electrolyte[2] | 1 | 2 | 2 | 2 | 2 |
| Fragrance | 1 | 1 | 1 | 1 | 1 |
| Water | 5 | 5 | 5 | 6 | 6 |
| Miscellaneous | Balance | Balance | Balance | Balance | Balance |
| Soap/Fatty Acid Chain length (% C12) | 25 | 30 | 30 | 30 | 29 |
| Bar Performance - Lather | | | | | |
| Flash Soil Lather | 3.0 | 1.0 | 2.0 | 3.0 | 3.0 |
| Ultimate Soil Lather | 4.5 | 2.0 | 3.0 | 4.5 | 4.5 |
| Wear Rate (g/rub) | 0.17 | 0.13 | 0.13 | 0.15 | 0.18 |
| Percent of wax (Paraffin) greater than 16 μm | 0 | 0 | 42 | 3 | 10 |
| Clinical Mildness Difference vs. C.E. 1 (p-value) | | | | | |
| Dryness | — | −0.25(0.05) | 0.07(0.63) | −0.28(0.01) | −0.20(0.05) |
| Redness | — | −0.07(0.65) | 0.05(0.66) | −0.18(0.10) | −0.05(0.64) |

[1]All examples, except C. E. 1 and C. E. 9 contain sodium topped coconut isethionate.
[2]$Na_2SO_4$ and NaCl

Comparative Example 1 (C. E. 1)

Comparative Example 1 (C. E. 1) is a marketed personal cleansing bar. It is comprised of primarily sodium acyl isethionate, fatty acid and soap. It does not contain the solid waxes of this invention. It has acceptable lather grades of 3.0/4.5. All mildness data are referenced vs. C. E. 1. C.E. 1 and C. E. 9 are standards for mild bars. They are equal to each other for mildness.

Example 2 vs. Experimental Example 3

These examples illustrate the enhanced mildness with a smaller size distribution of solid wax. These examples also show that sodium alkyl glyceryl ether sulfonate is more conducive to the formation of these particles than sodium acyl isethionate.

Example 2 is an alkyl glyceryl ether sulfonate (AGS) based personal cleansing bar. It contains high levels of AGS (34 parts), magnesium soap (17 parts), and paraffin (17 parts). At least 90% of the wax particles are sized between 0.1 and 1.6 microns. None of the wax particles are greater than C. E. 1. Neither of these results is significant with a p-value of less than 0.10. E. E. 3 has larger wax particles than Ex. 2 and is significantly less mild.

Example 4 vs. Example 5

These examples also illustrate the enhanced mildness with the smaller size of solid wax. These examples also show that magnesium soap is more conducive to the formation of these smaller paraffin particles than sodium acyl isethionate.

Example 4 is an alkyl glyceryl ether sulfonate (AGS)/acyl isethionate based personal cleansing bar. It contains high levels of AGS (17 parts), sodium acyl isethionate (17 parts), magnesium soap (17 parts), and paraffin (17 parts). It has lather grades of 3.0/4.5. At least 90% of the wax particles are sized between 0.2 and 7.3 microns. Only 3% of the wax particles are greater than 16 microns. It is 0.28 units less drying than C. E. 1 and 0.18 units less reddening than C. E. 1 in clinical mildness testing. Both results are significant with a p-value less than or equal to 0.10.

Example 5 is similar in composition to Example 4 but has more sodium acyl isethionate (28 parts vs. 17 parts acyl isethionate in Example 4) and less magnesium soap (10 parts rs. 17 parts magnesium soap in Example 4). It has lather grades of 3.0/4.5. The wax particles, 90% of which are sized between 1.3 microns and 12.9 microns, are larger than the particles in Example 4. Only 10% of the wax particles are greater than 16 microns. Example 5 was 0.20 units less drying than C. E. 1 and 0.05 units less reddening than C. E. 1. The dryness result is significant with a p-value of less than 0.10.

Example 8 vs. Example 4

Example 8 is an alkyl glyceryl ether sulfonate (AGS)/acyl isethionate based personal cleansing bar. It contains high levels of AGS (18 parts), sodium acyl isethionate (18 parts), magnesium soap (18 parts), and paraffin (18 parts). Ex. 8 contains 1 part sodium isethionate. It has lather grades of 1.5/1.5. At least 90% of its wax particles are between 0.6 and 13.1 microns. Only 5 % of its wax particles are greater than

TABLE D

| Component | E.E. 6 | Ex. 7 | Ex. 8 | C.E. 9 |
|---|---|---|---|---|
| Na-Acyl Isethionate | 23 | 23 | 18 | 53 |
| Na-Alkyl Glyceryl Ether Sulfonate | 23 | 23 | 18 | — |
| Na-soap | 10 | 10 | 2 | 5 |
| Mg-soap | 4 | 4 | 18 | |
| Free Fatty Acid | 1 | 1 | 5 | 10 |
| Paraffin | 28 | 28 | 18 | 9 |
| Na-Isethionate | 1 | 1 | 1 | 5 |
| Glycerin | 4 | 4 | 4 | |
| Electrolyte | 2 | 2 | 2 | 1 |
| Fragrance | 1 | 1 | 1 | 1 |
| Water | 6 | 6 | 7 | 6 |
| Sodium Cetearyl Sulfate | — | — | — | 10 |
| Miscellaneous | Balance | Balance | Balance | Balance |
| Soap/Fatty Acid Chain length (% C12) | 20 | 20 | 75 | |
| Bar Performance - Lather | | | | |
| Flash Soil Lather | 3.0 | 3.5 | 1.5 | 2.5 |
| Ultimate Soil Lather | 5.0 | 5.0 | 1.5 | 3.0 |
| Wear Rate g/rub | 0.25 | 0.19 | 0.14 | 0.22 |
| Percent of wax (Paraffin) greater than 16 μm | 16 | 10 | 5 | 24 |
| Clinical Mildness Difference vs. C.E. 1 (p-value) | | | | |
| Dryness | 0.11(0.37) | −0.18(0.10) | −0.28(0.01) | 0.02(0.90) |
| Redness | 0.02(0.83) | −0.32(0.05) | −0.12(0.29) | 0.02(0.93) |

Experimental Example 6 vs. Example 7

These examples illustrate enhanced mildness via increasing the amount of small sized solid wax within the specified range. These examples also show that a longer crutcher mix time is more conducive to the formation of the smaller sized particles and therefore improves mildness of the finished bar.

Experimental Example 6 has lather grades of 3.0/5.0. Its crutcher mix time before drying and cooling is 1 hour. Too many of its paraffin particles (16%) are above 16 microns. It is directionally harsher than C. E. 1, 0.11 units more drying than C. E. 1 and 0.02 units more reddening than C. E. 1 in clinical mildness testing. E.E. 6 and Example 7 have identical compositions; but Example 7 is mixed for 4 hours and E.E. 6 is mixed for only 1 hour. Example 7 has lather grades of 3.5/5.0. At least 90 % of its wax particles are between 0.1 and 14.7 microns. Only 10% of the wax particles of Example 7 are greater than 16 microns. Ex. 7 is 0.18 units less in drying than C. E. 1 and 0.32 units less in reddening than C. E. 1. The dryness and redness results are significant with a p-value of less than 0.10. Ex. 7 has smaller particles than E.E. 6 and is milder.

16 microns. Example 8 is 0.28 units less in drying and 0.12 units less in reddening than C. E. 1. The dryness result is significant with a p-value less than or equal to 0.10.

Example 4 is an alkyl glyceryl ether sulfonate (AGS)/acyl isethionate based personal cleansing bar, similar in composition to Example 8. It contains high levels of AGS (17 parts), sodium acyl isethionate (17 parts), magnesium soap (17 parts), sodium isethionate (5 parts) and paraffin (17 parts). It has lather grades of 3.0/4.5. At least 90 % of its wax particles are sized between 0.2 and 7.3 microns. Only 3% of its wax particles are greater than 16 microns. Ex. 4 is 0.28 units less in drying than C. E. 1 and 0.18 units less in reddening than C. E. 1 in clinical mildness testing. Both results are significant with a p-value less than or equal to 0.10.

These Examples (4 and 8) show that a higher level of sodium isethionate is more conducive to the formation of smaller wax particles than lower levels of sodium isethionate. Ex. 4 has five times more sodium isethionate than Ex. 8. These Examples also illustrate that mildness is maintained, even at higher levels of C12 chain length in the soap and fatty acid composition. See Table D for details.

Comparative Example 9

Comparative Example 9 (C. E. 9) is a marketed personal cleansing bar. It is comprised of primarily sodium cocoyl isethionate, sodium cetearyl sulfate, paraffin, and fatty acid. About 24% of its solid wax particles are greater than 16 microns in size. It has acceptable lather grades of 2.5/3.0. It is not significantly different in mildness from C. E. 1, but has better smear. Comparative Example 1 (C. E. 1 ) and C. E. 9 are standard bars for mildness in the trade. The bars containing the small sized wax particles of the present invention have mildness advantages over these comparable bar products. The bars of the present invention, particularly, Example 4 are superior to C. E. 1 as well as C. E. 2.

Experimental Example 6 vs. Example 7 illustrate enhanced mildness via increasing the amount of small sized solid wax to within the specified range. Example 7 is a superior bar to that of Experimental Example 6, notwithstanding identical formulations. These examples also show that a longer crutcher mix time is more conducive to the formation of the small sized particles and therefore improves mildness of the finished bar.

What is claimed is:

1. A lathering personal cleansing bar composition comprising:
   a) from 20 parts to 90 parts of a lathering surfactant, wherein said lathering surfactant is selected from the group consisting of methyl acyl taurates, N-acyl glutamates, alkyl sulfosuccinates, alkyl phosphate esters, ethoxylated alkyl phosphate esters, trideceth sulfates, ethoxylated alkyl sulfates, alkyl amine oxides, betaines, sultaines, C12–C14 alkyl glyceryl ether sulfonate, C12–C18 acyl sarcosinate, sodium acyl isethionate, sodium isethionate, soaps, and mixtures thereof;
   b) from 10 to 50 parts of a plasticizer which comprises small-sized solid wax particles wherein at least 85% of said wax particles have a particle size of less than 16 microns; and
   c) from 3 to 30 parts era binder wherein said binder is selected from the group consisting of water, liquid water-soluble aliphatic polyol, polyethylene glycol, polypropylene glycol, and mixtures thereof.

2. The personal cleansing bar of claim 1 wherein said wax particles have a melting point of from 41° C. to 82° C.

3. The personal cleansing bar of claim 2 wherein the plasticizer comprises small sized solid wax particles wherein at least 90% of said wax particles are less than 16 microns; and wherein the small sized solid wax particles are selected from the group consisting of beeswax, spermaceti, carnuba, bayberry, candelilla, montan, ozokerite, ceresin, paraffin, synthetic wax, microcrystalline wax, and mixtures thereof.

4. The personal cleansing bar of claim 3 wherein at least 90% of said wax particles are from 0.2 to 10 microns in size.

5. The personal cleansing bar of claim 4 wherein said wax particles consist essentially of paraffin.

6. The personal cleansing bar of claim 5 which comprises from about 20 to about 45 parts plasticizer.

7. A lathering personal cleansing bar compositions comprising:
   a) from 10 parts to 50 parts of small sized solid wax particles, wherein at least 85% of said wax particles have a particle size of less than 16 microns;
   b) from 20 parts to 90 parts era lathering surfactant:
   c) from 2 to 20 parts fatty acid;
   d) from 4 to 20 parts water;
   e) from 1 to 20 parts sodium soap;
   f) from 1 to 30 parts magnesium soap;
   g) from 0.1 to 10 parts sodium isethionate; and
   h) from 0 to 5 parts sodium chloride.

8. The personal cleansing bar of claim 7 wherein at least 90% of said wax particles have a particle size of less than 16 microns.

9. A lathering personal cleansing bar compositions comprising:
   a) from 10 parts to 50 parts of small sized solid wax particles, wherein at least 85% to 100% of said wax particles have a particle size of less than 16 microns;
   b) from 0 to 70 parts of sodium acyl isethionate;
   c) from 15 to 50 parts lathering mild synthetic surfactant, wherein said mild lathering surfactant is selected from the group consisting of methyl acyl taurates, N-acyl glutamates, alkyl sulfosuccinates, alkyl phosphate esters, ethoxylated alkyl phosphate esters, trideceth sulfates, ethoxylated alkyl sulfates and alkyl amine oxides, betaines, sultaines, C12–C14 alkyl glyceryl ether sulfonate, C12–C18 acyl sarcosinate, and mixtures thereof,
   d) from 2 to 20 parts fatty acid;
   e) from 4 to 20 parts water;
   f) from 1 to 20 parts sodium soap;
   g) from 1 to 30 parts magnesium soap;
   h) from 0.1 to 10 parts sodium isethionate; and
   i) from 0 to 5 parts sodium chloride.

10. The personal cleansing bar of claim 9 wherein at least 90% of said wax particles have a particle size of less than 16 microns.

11. The personal cleansing bar of claim 10 which comprises from about 15 to about 50 parts sodium acyl isethionate.

12. The personal cleansing bar of claim 11 which has a pH ranging from 4.0 to 10.0.

* * * * *